United States Patent [19]
Maracas

[11] Patent Number: 6,060,023
[45] Date of Patent: May 9, 2000

[54] MOLECULAR SENSING APPARATUS

[75] Inventor: George N. Maracas, Phoenix, Ariz.

[73] Assignee: Motorola, Inc., Schaumburg, Ill.

[21] Appl. No.: 09/052,559

[22] Filed: Mar. 31, 1998

[51] Int. Cl.[7] .......................... G01N 15/06; G01N 1/14; G01N 33/53; G01N 25/18; A61K 38/00

[52] U.S. Cl. .................. 422/68.1; 422/50; 422/55; 422/56; 422/58; 422/63; 422/69; 422/76; 422/81.02; 422/81.03; 422/81.05; 422/81.07; 422/91.2; 435/4; 435/5; 435/6; 435/7.1; 435/7.2; 435/7.9; 435/90; 435/91.1; 435/91.3; 435/91.5; 435/91.51; 435/173.1; 436/149; 436/150; 436/806; 436/807; 530/300; 530/350; 530/333; 530/388.1

[58] Field of Search ................... 422/50, 55, 56, 422/68.1, 57, 58, 63, 69, 76, 81.02, 81.03, 81.05, 81.07, 91.2; 435/4, 5, 6, 7.1, 7.2, 7.9, 90, 91.1, 91.3, 91.5, 91.51, 173.1; 436/149, 150, 806, 807; 530/300, 350, 333, 388.1

[56] References Cited

U.S. PATENT DOCUMENTS

| | | | |
|---|---|---|---|
| 5,605,662 | 2/1997 | Heller et al. | 422/68.1 |
| 5,620,850 | 4/1997 | Bamdad et al. | 530/300 |
| 5,653,939 | 8/1997 | Hollis et al. | 422/50 |

FOREIGN PATENT DOCUMENTS

| | | | |
|---|---|---|---|
| WO 93/22678 | 11/1993 | WIPO | G01N 1/14 |

OTHER PUBLICATIONS

Williams et al., Studies of Oligoonucleotide interactions by hybridisation to Array: influence of dangling ends on duplex yield, Nucleic Acids Research 8:1365–1367 (1994) Mar. 9, 1994.

Gardner et al., Application of conducting polymer technology in microsystems, Sensors and Actuators 51:57–66 (1995) Feb. 8, 1995.

Boguslavsky et al., Applications of redox polymers in biosensors, Solid State Ionics 60:189–197 (1993) Aug. 1, 1993.

"Effect of Guest/Host Interactions on Photoinduced Electron Transfer Reactions", Claudia Turro, Inorg. Chim. Acta (1996), 252(112), 333–338 CODEN: ICHAA3; ISSN: 0020–1693 Abstract.

"Oxidative DNA Damage through Long–Range Electron Transfer", Daniel B. Hall et al., Nature (London) (1996), 382(6593), 731–735. CODEN: NATUAS; ISSN: 0028–0836 Abstract.

"Site–specific Nucleic Acid Recognition", Cynthia M. Dupureur et al., Compr. Supramol. Chem (1996), vol. 5, 295–315. Editor(s): Suslick, Kenneth S. Publisher: Elsevier, Oxford, UK, CODEN: 63GFA6 Abstract.

Rates of DNA Mediated Electron Transfer between Metallointercalators, M.R. Arkin et al, Science (Washington, D.C.) (1996) 273(5274), 475–480, CODEN; SCIEAS; ISSN; 0036–8075 Abstract.

(List continued on next page.)

*Primary Examiner*—James C. Housel
*Assistant Examiner*—Gailene R. Gabel
*Attorney, Agent, or Firm*—James E. Gauger

[57] ABSTRACT

A molecular sensing apparatus comprises a first electrode (10), a second electrode (12), a first molecule (20), a second molecule (22), and a third molecule (34). The first molecule (20) has a first chain of nucleic bases (30) and a first group (24). The first group (24) is bound to the first electrode (10). The second molecule (22) has a second chain of nucleic bases (32) and a second group (26). The second group (26) is bound to the second electrode (12). The third molecule (34) is bound to the first molecule (20) and the second molecule (22). A method which uses the molecular sensing apparatus is disclosed.

17 Claims, 4 Drawing Sheets

OTHER PUBLICATIONS

"Oxidative DNA Damage by a Rhodium Intercalator through Long Range Photoinduced Electron Transfer", Daniel B. Hall, Book of Abstracts, 212th ACS National Meeting, Orlando, FL, Aug. 25–29 (1996), INOR–351 Publisher; American Chemical Society, Washington, D.C. CODEN; 63BFAF Abstract.

"The Development of a Synthetic Nuclease: DNA Hydrolysis by a Rhodium Intercalator Containing a Tethered Peptide", M.P. Fitzsimons, Book of Abstracts, 212th ACS National Meeting, Orlando, FLA, Aug. 25–29 (1996), INOR–330 Publisher; American Chemical Society, Washington, D.C. CODEN; 63BFAF Abstract.

"Rhodium Intercalators with Appended Peptides: Recognition and Reaction", J.K. Barton et al., Book of Abstracts, 212th ACS National Meeting, Orlando, FLA, Aug. 25–29 (1996), INOR–179 Publisher; American Chemical Society, Washington, D.C. CODEN; 63BFAF Abstract.

"Excited State Properties of Rh(phi)2(phen)3+ and Related Complexes: a Strong Photooxidant", Claudia Turro et al., Inorg. Chim. Acta (1996), 243(1–2), 101–108. CODEN; ICHAA3; ISSN: 0020–1693 Abstract.

"OS(phen)2dppz2+ in Photoinduced DNA–Mediated Electron Transfer Reactions", R. Erik Holmlin et al, Am. Chem. Soc. (1996), 118(22), 5236–5244. CODEN; JACSAT; ISSN: 0002–7863 Abstract.

"Electron Transfer between Metal Complexes Bound to DNA: is DNA a Wire?", Eric D.A. Stemp et al., Met. Ions Bio. Syst. (1996), 33 (Probing of Nucleic Acids by Metal Ion Complexes of Small Molecules), 325–365. CODEN: MIBSCD; ISSN: 0161–5149 Abstract.

"Recognition of DNA by Octahedral Coordination Complexes", Timothy W. Johann et al., Philos. Trans. R. Soc. London, Ser. A (1996), 354(1706) 299–324, CODEN: PTRMAD; ISSN: 0962–8428 Abstract.

"Recognition of Nucleic Acids by Transition Metal Complexes", Ayesha Sitlani et al., Handbook Met–Ligand Interact. Biol. Fluids: Bioinorg. Chem. (1995), vol. 1, 466–87. Editor(s): Berthon, Guy. Publisher Dekker, New York, NY CODEN:620XAP Abstract.

"Luminescence Quenching in Supramolecular Systems: A Comparison of DNA–and SDS Michelle–Mediated Photoinduced Electron Transfer between Metal Complexes", M.R. Arkin et al., J. Am. Chem. Soc (1996), 118(9), 2267–74. CODEN: JACSAT; ISSN: 0002–7863 Abstract.

"Intractions Between DNA–Iintercalated Metal Complexes: Evidence for Rapid Long–Range Electron Transfer?", Eric J.C. Olson, Book of Abstracts, 210th ACS National Meeting, Chicago, IL, Aug. 20–24 (1995), Issue Pt. 2, PHYS–344 Publisher: American Chemical Society, Washington, D.C. CODEN: 61XGAC Abstract.

"Long Range Electron Transfer between Metallointercalators bound to DNA", Erik D.A. Stemp, Book of Abstracts, 210th ACS National Meeting, Chicago, IL, Aug. 20–24 (1995), Issue Pt. 2 PHYS–253 Publisher: American Chemical Society, Washington, D.C. CODEN 61XGAC Abstract.

"Photoinduced Electron Transfer of Rh(III) Complexes with Donors, Acceptors, and DNA", Claudia Turro, Book of Abstracts, 210th ACS National Meeting, Chicago, IL, Aug. 20–24 (1995), Issue Pt. 1 INOR–168C Publisher: American Chemical Society, Washington, D.C. CODEN 61XGAC Abstract.

"Metallointercalators as Probes of the DNA Way" Michelle R. Arkin et al, Adv. Chem. Ser. (1995) 246(Mechanistic Bioinorgnic Chemistry), 449–69, CODEN; ADCSAJ; ISSN; 0065–2393 Abstract.

"Structural Examination of Enantioselective Intercalation: 1H NMR of Rh(en)2phi3+ Isomers Bound to d(GTGCAC)2", Thomas P. Shields, Biochemistry (1995), 34(46), 15049–56. CODEN: BICHAW; ISSN: 0006–2960 Abstract.

"Sequence–Selective DNA Recognition and Photocleavage: A Comparison of Enantiomers of Rh(en) 2phi3+", Thomas P. Shields, Biochemistry (1995), 34(46), 15037–48, CODEN: BICHAW; ISSN: 0006–2960 Abstract.

"1H NMR Structural Evidence for the Sequence–Specific Design of an Intercalator: [Rh[R,R,)–Me2trien]phi]3+ Bound to d(GAGTGCACTC)2", Brian P. Hudson, J. Am. Chem. Soc. (1995), 117(36), 9379–80. CODEN: JACSAT; ISSN: 0002–7863 Abstract.

"Proton Transfer Quenching of the MLCT Excited State of Ru(phen)2dppz2+ in Homogeneous Solution and Bound to DNA", Claudia Turro et al, J. Am. Chem Soc. (1995), 117(35), 9026–32. CODEN: JACSAT; ISSN: 0002–7863 Abstract.

"Long–Range Photoinduced Electron Transfer Mediated by the DNA Double Heliz", Michelle Arkin et al., Polym. Mater. Sci. Eng (1994), 71, 598–9. CODEN; PMSEDG; ISSN: 0743–0515 Abstract.

"Sequence–Specific DNA Binding by a Rhodium Complex: Recognition Based on Sequence–Dependent Twistability", Robert H. Terbrueggen et al, Biochemistry (1995), 34(26), 8227–34. CODEN; BICHAW; ISSN: 0006–2960 Abstract.

"Construction of Coordinatively Saturated Rhodium Complexes Containing Appended Peptides", Niranjan Y. Sardesai et al, Bioconjugate Chem. (1995), 6(3), 302–12. CODEN: BCCHES; ISSN: 1043–1802 Abstract.

"Electron Transfer between Metallointercalators Bound to DNA: Spectral Identification of the Transient Intermediate", Eric D.A. Stemp et al, J. Am. Chem. Soc (1995), 117(8), 2375–6. CODEN: JACSAT; ISSN: 0002–7863 Abstract.

"Os(phen)2(dppz)2+: A Red–Emitting DNA Probe", Erick R. Holmlin et al, Inorg. Chem(1995), 34(1), 7–8, CODEN; INOCAJ; ISSN; 0020–1669 Abstract.

"Photoinduced Electron Transfer through the Double Helix: Is DNA a Wire?", Jacqueline K. Barton, 37th (40 Years of the DNA Double Helix) 171–9. CODEN; PRAWAC; ISSN; 0557–1588 Abstract.

"DNA Photofootprinting with Rh(phi)2bpy3+", Scott L. Klakamp et al, Methods Mol. Biol. (Totowa, N.J.) (1994), 31 (Protocols for Gene Analysis), 331–7. CODEN; MMBIED; ISSN: 1064–3745 Abstract.

"Fast Photoinduced Electron Transfer through DNA Intercalation", Catherine J. Murphy et al, Proc. Natl. Acad Sci. U.S.A. (1994), 91(12), 5315–19. CODEN: PNASA6; ISSN: 0027–8424 Abstract.

"Use of Selective Deuteration and 1H NMR in Demonstrating Major Groove Binding of Δ [Ru(phen)2dppz]2+ to d(GTCGAC)2", Cynthia M. Dupureur et al, J. Am. Chem. Soc. (1994), 116(22), 10286–7. CODEN: JACSAT; ISSN: 0002–7863 Abstract.

"1H–NMR of Rh(NH3) 4phi3+ Bound to d(TGGCCA)2: Classical Intercalation by a Nonclassical Octahedral Metallointercalator", J. Grant Collins et al, J. Am. Chem. Soc. (1994), 116(22), 9840–6. CODEN: JACSAT; ISSN: 0002–7863 Abstract.

"Sequence–Specific Recognition of DNA by Phenanthrenequinone Diimine Complexes of Rhodium(III): Importance of Steric and Van der Walls Interactions.", Ayesha Sitlanti et al, Biochemistry et al. (1994), 33(40), 12100–8. CODEN; BICHAW; ISSN: 0006–2960 Abstract.

"DNA Recognition by Peptide Complexes of Rhodium(III): Example of a Glutamate Switch", Niranjan Y. Sardesai et al, J. Am. Chem. Soc. (1994), 116(17), 7502–8. CODEN; JACSAT; ISSN: 0002–7863 Abstract.

"Rational Construction of Metallointercalators: Syntheses, Structures, and Characterizations of Isomers of (2S, 9S)–Diamino–4–7–diazadecane)(9,10–phenanthrenequinone Diimine) Rhodium(III)", Achim H. Krotz, et al., Inorg. Chem. (1994), 33(9), 1940–7, CODEN: INOCAJ; ISSN: 0020–1669.

"Correlations of Crystal Structures of DNA Oligonucleotides with Enantioselective Recognition by Rh(phen)2phi3+: Probes of DNA Propeller Twisting in Solution", Donna Campisi, et al, Biochemistry(1994) 33(14), 4130–9. CODEN: BICHAW; ISSN; 0006–2960 Abstract.

"Ruthenium Complexes an Luminescent Reporters of DNA", Catherine J. Murphy et al., Methods Enzymol (1993), 226(Metallobiochemistry, Pt. C), 576–94, 1 plate. CODEN; MENZAU; ISSN; 0076–6879 Abstract.

"Ligand–Specific Charge Localization in the MLCT Excited State of Ru(bpy)2(dpphen)2+ Monitored by Time–Resolved Resonance Raman Spectroscopy", Claudia Turro et al, Inorg. Chem. (1994), 33(7), 1344–7. CODEN; INOCAJ; ISSN; 0020–1669 Abstract.

"Metalointercalators: Syntheses, Structures, and Photochemical Characterizations of Phenanthrenequinone Diimine Complexes of Rhodium(III)", Achim H. Krotz et al., Inorg Chem. (1993), 32(26), 5963–74. CODEN; INOCAJ; ISSN; 0020–1669 Abstract.

"Long–range Photoinduced Electron Transfer through a DNA Helix", C.J. Murphy et al, Science (Washington, D.C., 1883) (1993),262(5136), 1025–9. CODEN; SCIEAS; ISSN: 0036–8075 Abstract.

"Assembly of DNA Recognition Elements on an Octahedral Rhodium Intercalator Predictive Recognition of 5'–TGCA–3' by Δ—[Rh(R,R)–Me2trien phi]3+" Achim H. Krotz et al, J. Am. Chem. Soc. (1993), 115(26), 12577–8, CODEN; JACSAT; ISSN: 0002–7863 Abstract.

"Enantiospecific Palindromic Recognition of 5'–d(CTCTA-GAG)–3' by a Novel Rhodium Intercalator: Analogies to a DNA–binding Protein", Ayesha Sitiani et al., J. Am. Chem. Soc. (1993), 115(26), 12589–90. CODEN: JACSAT; ISSN: 0002–7863 Abstract.

"Chemical Probing of tDNAPhe with Transition Metal Complexes: A Structural Comparison of RNA and DNA", Ai Ching Lim, et al, Biochemistry(1993) 32(41)11029–34. CODEN;BICHAW; ISSN: 0006–2960 Abstract.

"How to Make a Molecular Light Switch Sequence–Specific: Tethering of an Oligonucleotide to a Dipyridophenazine Complex of Ruthenium(II)", Yonchu Jenkins et al, Proc. SPIE–Int. Soc. Opt. Eng. (1993), 1885 (Proceedings of Advances in Fluorecence Sensing Technology, 1993), 129–37. CODEN:PSISDG; ISSN: 0277–786X Abstract.

"DNA Recognition by Rhodium(III) Polyamine Intercalators: Considerations of Hydrogen Bonding and Van der Waals Interactions" Achim H. Krotz et al., J. Am. Chem. Soc. (1993), 115(10), 3877–82. CODEN; JACSAT; ISSN: 0002–7863 Abstract.

"Mixed Ligand Complexes for Use as Luminescence Labels for Detection and Photochemical Cleavage of DNA", Jacqueline K. Barton, U.S. 87 pp. contin–in–part of U.S. 5,112,974. CODEN: USXXAM Abstract.

"Transition Metal Complexes as Probes of Nucleic Acids", Christine S. Chow, Methods Enzymol (1992, 212(DNA Struct., Pt. B), 219–42. CODEN; MENZAU; ISSN; 0076–6879 Abstract.

"A Sequence–Specific Molecular Light Switch: Tethering of an Oligonucleotide to a Dipyriodophenazine Complex of Ruthenium(II)", Jonchu Jenkins, J. Am. Chem. Soc. (1992), 114(22), 8736–8 CODEN; JACSAT; ISSN: 0002–7863 Abstract.

"Novel Dipyridophenazine Complexes of Ruthenium(II): Exploring Luminescent Reporters of DNA", Richard M. Hartshorn, et al, J. Am. chem. soc. (1992), 114(15), 5919–25 CODEN; JACSAT; ISSN;: 0002–7863 Abstract.

"Characterization of dipyridophenazine Complexes of Ruthenium(II): the Light Switch Effect as a Function of Nucleic Acid Sequence and Conformation", Yonchu Jenkins et al, Biochemistry(1992), 31(44), 10809–16. CODEN; BICHAW; ISSN: 0006–2960 Abstract.

"Protein Surface Recognition and Covalent Binding by Chromium Nitrilotriacetate Complexes: Elucidation using NMR and CD Spectroscopies", Jeffrey R. Bocarsly et al., Inorg. Chem. (1992), α 31(13), 2827–34. CODEN; INOCAJ; ISSN; 0020–1669 Abstract.

"Photoelectron transfer between molecules absorbed in restricted Spaces", Nicholas J. Turro, et al, Photochem. convers. Storage Sol. Energy, Proc. Int. Conf. 8th (1991), Meeting date 1990, 121–39. Editor(s): Pelizzetti, Ezio; Schiavello; Mario. Publisher: Kluwer, Dordrecht, Neth. CODEN; 570XAF Abstract.

"Recognition of G–U Mismatches by Tris(4,7–Diphenyl–1, 10–Phenanthroline) Rhodium(III)" Christine S. Chow, et al, Biochemistry (1992), 31(24), 5423–9. CODEN: BICHAW; ISSN: 0006–2960 Abstract.

"Delineation of Structural Domains in Eukaryotic 5S rRNA with a Rhodium Probe" Christine S. Chow, et al, Biochemistry (1992), 31(13), 3534–42. CODEN; BICAW; ISSN: 0006–2960 Abstract.

"DNA Photocleavage by Phenanthrenequinone Diimine Complexes of Rhodium(III): Shape–Selective Recognition and Reaction" Ayesha Sitiani et al, J. Am. Chem. Soc. (1992), 114(7), 2303–12. CODEN;JACSAT; ISSN: 0002–7863 Abstract.

"Recognition of Tertiary Structure in tRNAs by Rh(phen)2phi3+, a new Reagent for RNA Structure–function Mapping", Christine S. Chow, et al, Biochemistry (1992) CODEN; BICHAW; ISSN: 0006–2960 Abstract.

"Molecular Recognition and Chemistry in Restricted Reaction Spaces. Photophysics and Photoinduced Electron Transfer on the surfaces of Micelles, Dendrimers, and DNA", Nicholas J. Turro et al, Acc. chem. Res. (1991), 24(11), 332–40. CODEN; ACHRE4; ISSN: 0001–4842.

"Photoinduced Electron Transfer Quenching of Excited Ruthenium (() polypyridyls Bound to DNA: The Role of the Nucleic Acid Double Helix", Gullermo Orellana, Photochem. Photobiol. (1991), 54(4), 499–509 CODEN: PHCBAP; ISSN: 0031–8655 Abstract.

"Targeting DNA Sites with Simple Metal Complexes", Jacqueline K. Barton et al., Pept.: Chem., Struct. Biol. Proc. Am. Pept. Symp., 11th (1990), Meeting Date 1989, 785–94. Editor(s): Rivier, Jean E.; Marshall, Garland R. Publisher: ESCOM Sco. Pub., Leiden, Neth. CODEN; 56XTA7 Abstract.

"Probing Nucleic Acids with Transition Metal Complexes", Anna Marie Pyle et al, Prog. Inorg. Chem. (1990), 38, 413–75. CODEN: PIOCAR; ISSN; 0079–6379 Abstract.

Coordination Complexes and Uses Thereof as Binding Agents and Probes to DNA and as Neoplasm Inhibitors and Inhibitors of Human Immunodeficiency Virus (HIV), Jacqueline K. Barton, PCT Int. Appl. 63 pp. CODEN; PIXXD2. WO 9005732 A1 900531 Abstract.

"Probing Microstructures in Double–Helical DNA with Chiral Metal Complexes: Recognition of Changes in Base–Pair Propellar Twisting in Solution", Anna Marie Pyle. J. Am. Chem. Soc. (19900, 112(25), 9432–4. CODEN: JACSAT; ISSN: 0002–7863 Abstract.

"On Demonstrating DNA Intercalation", Eric C. Long et al. Acc. Chem. Res. (1990), 23(9), 271–3. CODEN: ACHRE4; ISSN: 0001–4842 Abstract.

"A Molecular Light Switch for DNA: Ru(bpy)2(dppz)2+", Alan E. Friedman et al., J. Am. Chem. Soc (1990), 112(12), 4960–2. CODEN; JACSAT; ISSN; 0002–7863 Abstract Only.

"Targeting DNA Sites with Chiral Metal Complexes", Jacqueline K. Barton, Pure Appl. Chem. (1989), 61(3), 563–4. CODEN; PACHAS; ISSN: 0033–4545 Abstract Only.

"Shape–Selective Targeting of DNA by Phenanthrenequinone Diiminerhodium (III) Photocleaving Agents", Anne Marie Pyle et al., J. Am. Chem. Soc. (1989), 111(12), 4520–2. CODEN; JACSAT; ISSN; 0002–7863 Abstract Only.

"Mixed–ligand Complexes of Ruthenium (II): Factors Governing Binding to DNA", A.M. Pyle et al., J. Am. Chem. Soc. (1989), 111(8), 3051–8. CODEN; JACSAT; ISSN; 0002–7863 Abstract Only.

"Recognizing DNA Structures", Jacqueline K. Barton, Chem. Eng. News (1988), 66(39), 30–42. CODEN; CENEAR; ISSN: 0009–2347 Abstract Only.

"Accelerated Electron Transfer Between Metal Complexes Mediated by DNA", Michael D. Purugganan, Science (Washington, D.C. 1883–) (1988), 241(4873), 1645–9. CODEN; SCIEAS; ISSN; 0036–8075 Abstract Only.

"Towards the Design of Synthetic Restriction Enzymes with Transition Metal Complexes", Jacqueline K. Barton, et al. Front. Chem (1989), 1(Biotechnology), 5–25. CODEN; FCBIE2: ISSN: 1047–0506 Abstract Only.

"Shape–Selective Cleavage of tRNAPhe by Transition Metal Complexes", Christine S., Chow et al., J. Am. Chem. Soc. (1990), 112(7), 2839–41. CODEN; JACSAT; ISSN; 0002–7863 Abstract Only.

MOLECULAR SENSING APPARATUS

TECHNICAL FIELD

The present invention relates to molecular sensing methods and systems.

BACKGROUND OF THE INVENTION

Recent efforts have been directed in developing chips for molecular detection. Of particular interest are DNA chips for sequencing and diagnostic applications. A DNA chip includes an array of chemically-sensitive binding sites having single-stranded DNA probes or like synthetic probes for recognizing respective DNA sequences. A sample of single-stranded DNA is applied to all of the binding sites of the DNA chip. The DNA sample attaches to DNA probes at one or more of the binding sites. The sites at which binding occurs are detected, and one or more molecular structures within the sample are subsequently deduced.

In sequencing applications, a sequence of nucleotide bases within the DNA sample can be determined by detecting which probes have the DNA sample bound thereto. In diagnostic applications, a genomic sample from an individual is screened with respect to a predetermined set of probes to determine if the individual has a disease or a genetic disposition to a disease.

Present molecular detection devices are better equipped to sense an aggregate sample of DNA/RNA rather than individual DNA/RNA strands. The ability to sense individual DNA/RNA strands (which may be either single-stranded or double-stranded) would advantageously reduce the DNA/RNA sample size that is applied to the device for detection purposes.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Figure 1:
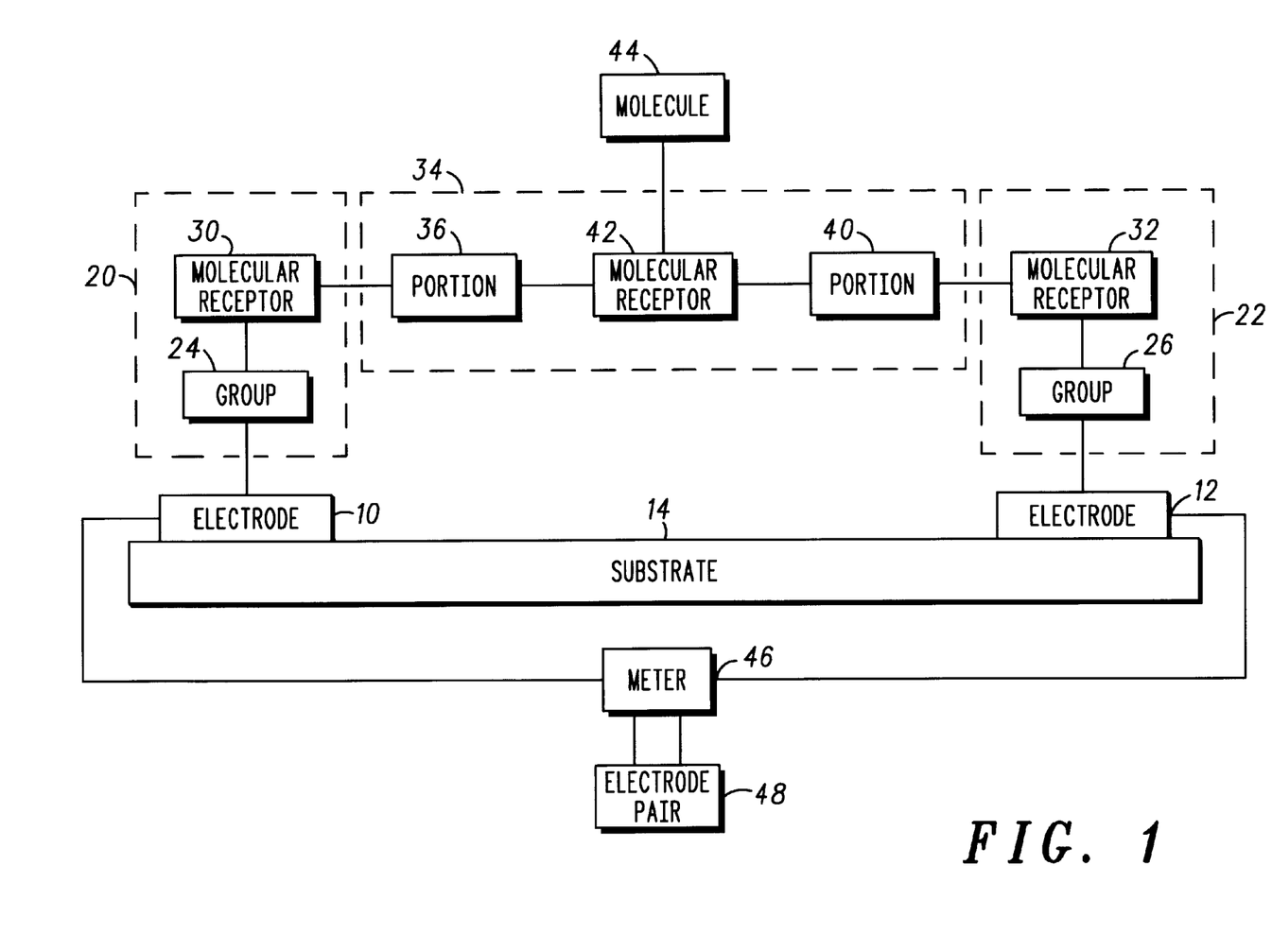
FIG. 1 is a block diagram of a molecular sensing apparatus in accordance with the present invention.

FIG. 1 is a block diagram of a molecular sensing apparatus in accordance with the present invention. The molecular sensing apparatus includes a first electrode 10 and a second electrode 12 supported by a substrate 14. A first molecule 20 is bound to the first electrode 10. A second molecule 22 is bound to the second electrode 12.

The first molecule 20 includes an electrically-conductive group 24 which binds to a surface of the first electrode 10.

Preferably, the group 24 includes an end group comprising either sulfur, selenium, or tellurium, to bind to the first electrode 10, or a silane group for binding to oxide surfaces.

Similarly, the second molecule 22 includes an electrically-conductive group 26 which binds to a surface of the second electrode 12. Preferably, the group 26 includes an end group comprising either sulfur, selenium, or tellurium, to bind to the second electrode 12, or a silane group for binding to oxide surfaces.

The first molecule 20 further includes a molecular receptor 30 coupled to the group 24. The molecular receptor 30 is receptive to a molecule having a predetermined and/or a preselected molecular structure. The molecular receptor 30 can include either a biological molecule or a synthetic molecule having a specific affinity to its corresponding molecule.

Preferably, the molecular receptor 30 includes a first chain of nucleic bases to hybridize with a molecule having a complementary chain of nucleic bases. In this case, the molecular receptor 30 can include a single strand of DNA (deoxyribonucleic acid), a single strand of PNA (peptide nucleic acid), a single strand of RNA (ribonucleic acid), an oligonucleotide, or a polynucleotide. Preferably, the molecular receptor 30 includes a PNA receptor because of its higher binding stability per unit length in comparison to DNA.

The second molecule 22 further includes a molecular receptor 32 coupled to the group 26. As with the molecular receptor 30, the molecular receptor 32 is receptive to a molecule having a predetermined and/or a preselected molecular structure, and can include either a biological molecule or a synthetic molecule having a specific affinity to its corresponding molecule.

Preferably, the molecular receptor 32 includes a second chain of nucleic bases to hybridize with a molecule having a complementary chain of nucleic bases. In this case, the molecular receptor 32 can include a single strand of DNA, a single strand of PNA, a single strand of RNA, an oligonucleotide, or a polynucleotide. Preferably, the molecular receptor 32 includes a PNA receptor because of its higher binding stability per unit, length in comparison to DNA.

The first molecule 20 and the second molecule 22 can be equivalent. Here, the group 24 is the same as the group 26, and the molecular receptor 30 is the same as the molecular receptor 32. In this case, it is preferred that the molecular receptor 30 has a sequence of the nucleic bases equivalent to a sequence of the nucleic bases for the molecular receptor 32.

Alternatively, the first molecule 20 and the second molecule 22 can differ. In this case, it is preferred that, the molecular receptor 30 differs from the molecular receptor 32 while the group 24 is the same as the group 26. Preferably, the molecular receptor 30 has a sequence of nucleic bases that differs from a sequence of nucleic bases for the molecular receptor 32.

A third molecule 34 is bound to the first molecule 20 and the second molecule 22. To bind to the first molecule 20, the third molecule 34 includes a first portion having an affinity to the molecular receptor 30. Preferably, the third molecule 34 includes a chain of nucleic bases 36 complementary to the first chain of nucleic bases in the molecular receptor 30. Similarly, to bind to the second molecule 22, the third molecule 34 includes a second portion having an affinity to the molecular receptor 32. Preferably, the third molecule 34 includes a chain of nucleic bases 40 complementary to the second chain of nucleic bases in the molecular receptor 32.

The third molecule 34 further includes a molecular receptor 42 interposed between the chain of nucleic bases 36 and the chain of nucleic bases 40. In general, the molecular receptor 42 is receptive to a molecule having a predetermined and/or a preselected molecular structure, and can include either a biological molecule or a synthetic molecule having a specific affinity to its corresponding molecule.

Preferably, the molecular receptor 42 includes a third chain of nucleic bases to hybridize with a molecule having a complementary chain of nucleic bases. In this case, the molecular receptor 42 can include a single strand of DNA, a single strand of PNA, a single strand of RNA, an oligonucleotide, or a polynucleotide.

The apparatus can be used to electrically sense for a binding event between a fourth molecule 44 and the molecular receptor 42 of the third molecule 34. Of particular interest are cases in which the fourth molecule 44 includes a single strand of DNA, a single strand of PNA, a single strand of RNA, an oligonucleotide, or a polynucleotide. For a specific binding event, the fourth molecule 44 has a chain of nucleic bases complementary to the third chain of nucleic bases.

A meter 46 is electrically connected to the first electrode 10 and the second electrode 12. The meter 46 is used to electrically detect a binding event between the fourth molecule 44 and the molecular receptor 42 of the third molecule 34. Preferably, the meter 46 includes an impedance meter, such as a resistance meter, a conductance meter, a capacitance meter or an inductance meter, to measure and/or detect a change in impedance between the first electrode 10 and the second electrode 12 resulting from the binding event.

Generally, the meter 46 can detect a change in an electrical quantity (measured between the first electrode 10 and the second electrode 12) between two instances of time (e.g. a pre-binding time and a post-binding time). Examples of the electrical quantity include, but are not limited to, charge, current, voltage, and impedance. The electrical quantity can be an AC (alternating current) quantity, a DC (direct current) quantity, or a combination of AC and DC.

Alternatively, the meter 46 can detect a change in an electrical quantity between a first electrode pair (comprising the first electrode 10 and the second electrode 12) and a second electrode pair 48. The second electrode pair 48 can have molecules equivalent to the first electrode 20, the second molecule 22, and the third electrode 34. However, a molecule such as the fourth molecule 44 is not exposed to these like molecules.

The meter 46 can be either integrated entirely to the substrate 14 (e.g. in a form an on-chip circuit), or entirely external to the substrate 14 (in a form of an off-chip circuit), or partially integrated to the substrate 14 and partially external to the substrate (e.g. using both on-chip and off-chip circuits).

In some cases, it may be preferred that the binding energy of the third molecule 34 to each of the first molecule 20 and the second molecule 22 be greater than the binding energy of the fourth molecule 44 to the third molecule 34. For this purpose or to satisfy other stability requirements, the length (based upon a number of bases) of each of the molecular receptors 30 and 32, and the portions 36 and 40 may be selected to be greater than the length of the molecular receptor 42 and optionally the length of the molecule 44. The use of PNA/PNA binding between the third molecule 34 and each of the first molecule 20 and the second molecule 22, and PNA/DNA or PNA/RNA binding between the third molecule 34 and the fourth molecule 44 also serve the aforementioned purpose. It is also preferred in some cases that the binding energy between the first molecule 20 and the electrode 10 and between the second molecule 22 and the electrode 12 be greater than the binding energy of the fourth molecule 44 to the third molecule 34. Satisfying all of these binding energy conditions is beneficial in cases where dehybridization of the fourth molecule 44 from the third molecule 34 is to be performed without detaching elements of the molecular sensor.

Figure 2:
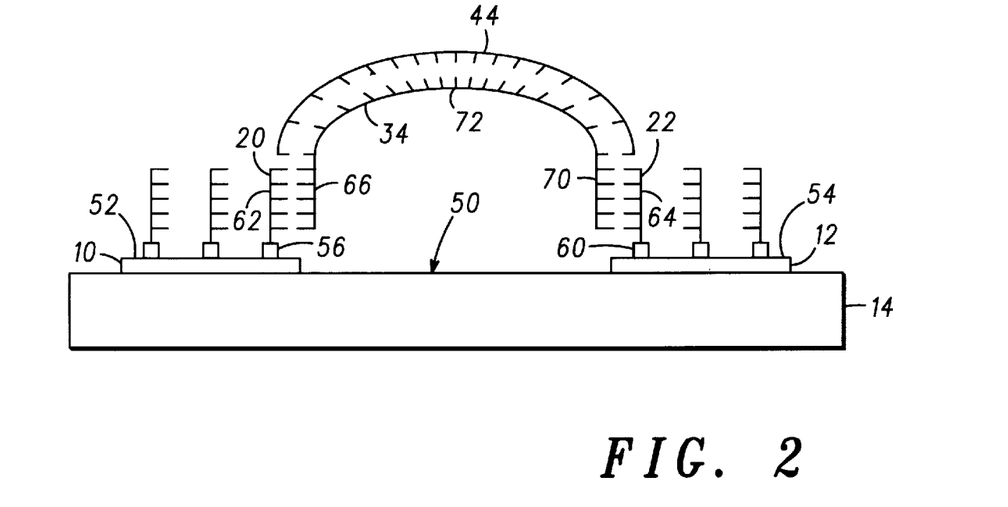
FIG. 2 is an illustration of a preferred embodiment of the molecular sensing apparatus of FIG. 1.

FIG. 2 is an illustration of a preferred embodiment of the molecular sensing apparatus of FIG. 1. The first electrode 10 and the second electrode 12 are integrated at a face 50 of the substrate 14. Preferably, the substrate 14 for thiol bind chemistries is metalized with a layer of gold to form the first electrode 10 and the second electrode 12. A standard mask such as an FET (field-effect transistor) mask can be used to fabricate the first electrode 10 and the second electrode 12 in this manner. Electrode contact patterns can be formed by several techniques, including but not limited to photolithography, electron beam lithography, scanning tunneling microscopy, and elastomeric contact printing.

A plurality of like molecules including the first molecule 20 are attached to the first electrode 10. Similarly, a plurality of like molecules including the second molecule 22 are attached to the second electrode 12.

The first electrode 10 has a surface 52 at which the first molecule 20 is bound. The second electrode 10 has a surface 54 at which the second molecule 22 is bound. Preferably, the surface 52 and the surface 54 are generally coplanar. Generally, the surface 52 and the surface 54 are closer to parallel than perpendicular, and have portions offset the same distance from the substrate 14. It is noted that the surface 52 and the surface 54 need not be generally coplanar. A non-coplanar alternative is subsequently described with reference to FIG. 5.

The first molecule 20 has an end group 56 of either sulfur, selenium, or tellurium to form a conjugate with the surface 52 of the first electrode 10. Similarly, the second molecule 22 has an end group 60 of either sulfur, selenium, or tellurium to form a conjugate with the surface 54 of the second electrode 12.

The first molecule 20 has an oligonucleotide 62 coupled to the end group 56. Similarly, the second molecule 22 has an oligonucleotide 64 coupled to the end group 60. Preferably, each of the oligonucleotides 62 and 64 has a length of about 8 to 10 bases, but can be longer depending on the desired temperature stability requirements.

The third molecule 34 has a first end portion 66 complementary to the oligonucleotide 62 and a second end portion 70 complementary to the oligonucleotide 64. Interposed between the first end portion 66 and the second end portion 70 is a polynucleotide 72. The polynucleotide 72 has a base sequence complementary to a sequence to be detected in the fourth molecule 44.

It is noted that the use of the first molecule 20 and the second molecule 22 is not necessary in alternative embodiments. In this case, the third molecule 34 is absent of the portions 36 and 40, but include end groups such as the end groups 24 and 26 to bind directly to the electrodes 10 and 12, respectively.

The molecules 20, 22, and 34 may be connected across various terminals of an active device such as either a field effect transistor, a bipolar junction transistor, or a single electron device to detect a binding event with the fourth molecule 44. For example, the electrodes 10 and 12 can be electrically connected to a drain and a source, respectively, or to a gate and a drain, respectively, of a field effect transistor. Alternatively, the electrodes 10 and 12 can be electrically connected to a base and an emitter, respectively, or to an emitter and a collector, respectively of a bipolar junction transistor. The selection of the active device is dependent upon the desired detection sensitivity and the external detection circuitry.

One or more of the molecules 20, 22, and 34 can be integrated directly onto terminals of the aforementioned transistors. The use of end groups 24 and 26 that bind to oxides and other insulators facilitate integration with MOS (metal oxide semiconductor) devices. A front-end comprised of the molecules and the transistor can be integrated with either an on-chip circuit or to off-chip circuits included in the meter 46. On-chip integration of one or more of the molecules 20, 22, and 34 with active transistors may enable low-noise, high-sensitivity detection of molecular events.

Figure 3:
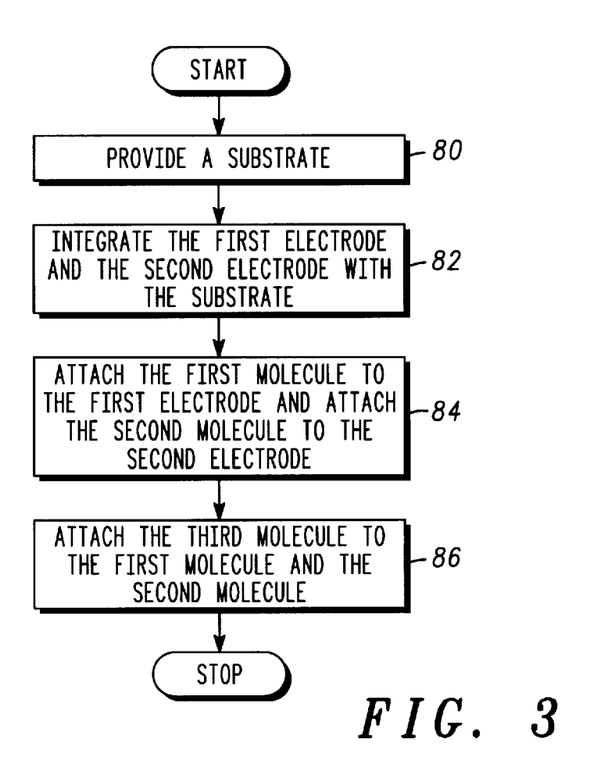
FIG. 3 is a flow chart summarizing steps performed in making a molecular sensing apparatus.

FIG. 3 is a flow chart summarizing steps performed in making a molecular sensing apparatus. The steps are described for the elements described with reference to FIG. 1 and FIG. 2.

As indicated by block 80, a step of providing the substrate 14 is performed. Thereafter, a step of integrating the first electrode 10 and the second electrode 12 with the substrate 14 is performed as indicated by block 82.

As indicated by block 84, steps of attaching the first molecule 20 to the first electrode 10 and attaching the second molecule 22 to the second electrode 12 are performed. Either the first molecule 20 is attached first, the second molecule 22 is attached first, or the first molecule 20 and the second molecule 22 are attached substantially simultaneously. The first molecule 20 and the second molecule 22 can be included in a common solution applied to the electrodes 10 and 12. Alternatively, the first molecule 20 and the second molecule 22 can be included in separate solutions.

As indicated by block 86, a step of attaching the third molecule 34 to the first molecule 20 and the second molecule 22 is performed. Preferably, the step of attaching the third molecule 34 is performed after the first molecule 20 is attached to the first electrode 10 and after the second molecule 22 is attached to the second electrode 12.

Figure 4:
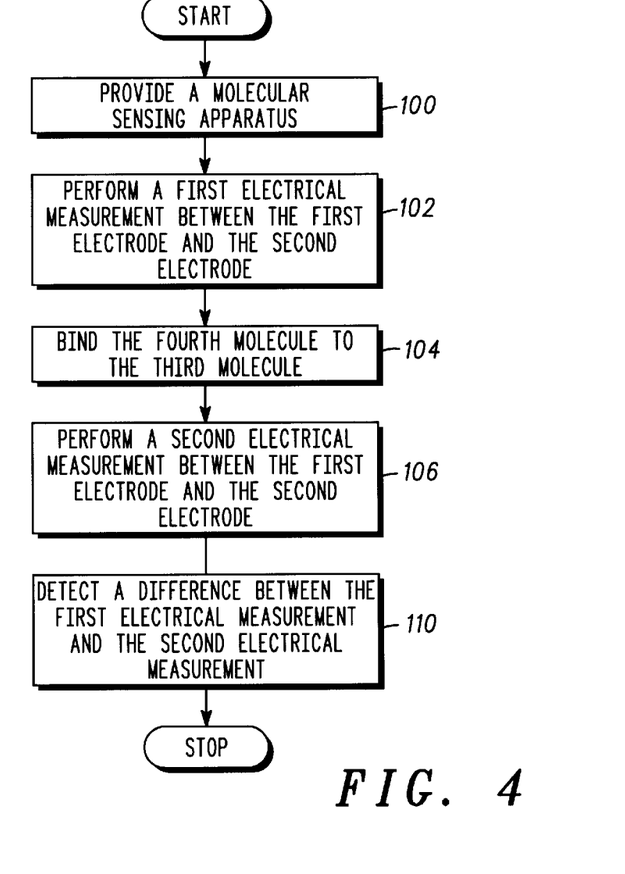
FIG. 4 is a block diagram of an embodiment of a molecular sensing method.

FIG. 4 is a block diagram of an embodiment of a molecular sensing method. As indicated by block 100, the method includes a step of providing a molecular sensing apparatus. Preferably, the molecular sensing apparatus is in accordance with embodiments described with reference to FIG. 1, FIG. 2, and FIG. 5.

As indicated by block 102, the method includes a step of performing a first electrical measurement between the first electrode 10 and the second electrode 12. The first electrical measurement is performed using the meter 46. Preferably, this step includes measuring a first conductance between the first electrode 10 and the second electrode 12.

As indicated by block 104, a step of binding the fourth molecule 44 to the third molecule 34 is performed. This step can include applying a solution including the fourth molecule 44 to the apparatus. Preferably, the step of binding the fourth molecule 44 to the third molecule 34 is performed after the step of performing the first electrical measurement.

As indicated by block 106, the method includes a step of performing a second electrical measurement between the first electrode 10 and the second electrode 12. The second electrical measurement is performed using the meter 46. Preferably, this step includes measuring a second conductance between the first electrode 10 and the second electrode 12. It is also preferred that the second electrical measurement be performed after the fourth molecule 44 is bound to the third molecule 34.

As indicated by block 110, a step of detecting a difference between the first electrical measurement and the second electrical measurement is performed. Preferably, this step can include detecting a difference in conductance that exceeds a predetermined threshold. The difference is indicative of a binding event between the fourth molecule 44 and the third molecule 34.

Figure 5:
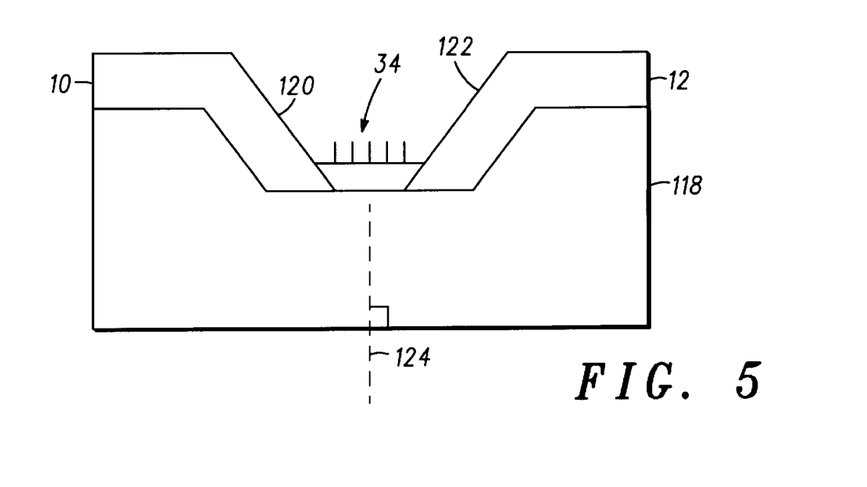
FIG. 5 is an illustration of an alternative embodiment of the molecular sensing apparatus of FIG. 1.

FIG. 5 is an illustration of an alternative embodiment of the molecular sensing apparatus of FIG. 1. In this embodiment, the first electrode 10 and the second electrode 12 have a V-shaped configuration. The V-shaped configuration is fabricated by reactive ion etching, selective crystallographic plane etching, or selective patterned epitaxial growth to a substrate 118 such as Si or GaAs. Preferably, the first electrode 10 and the second electrode 12 are formed of gold or are comprised of a semiconducting material such as indium arsenide.

The first electrode 10 has a surface 120 to which a first end of the third molecule 34 is attached. The first end of the third molecule 34 have an end group which is directly attached to the surface 120. Alternatively, the third molecule 34 is bound to the first molecule 20 which is directly attached to the surface 120 as described earlier. The second electrode 12 has a surface 122 to which a second end of the third molecule 34 is attached. The second end of the third molecule 34 have an end group which is directly attached to the surface 122. Alternatively, the third molecule 34 is bound to the second molecule 22 which is directly attached to the surface 122 as described earlier.

Both the surface 120 and the surface 122 are transverse to a generally planar orientation of the substrate 118. The planar orientation of the substrate 118 is represented a normal axis 124.

The embodiment described with reference to FIG. 5 can be used in performing the molecular sensing method of FIG. 4.

Figure 6:
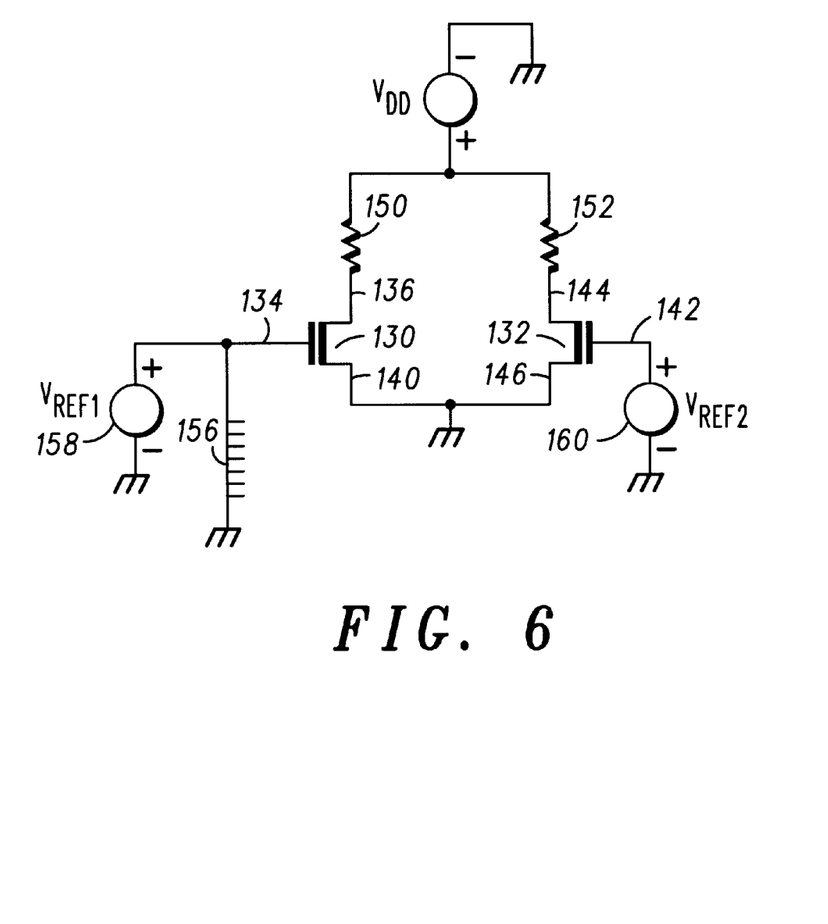
FIG. 6 is a schematic diagram of an embodiment of a circuit used in the meter for molecular sensing.

FIG. 6 is schematic diagram of an embodiment of a circuit used in the meter 46 for molecular sensing. The circuit comprises a first transistor 130 and a second transistor 132. The first transistor 130 includes a gate 134, a drain 136, and a source 140. The second transistor includes a gate 142, a drain 144, and a source 146. A first resistor 150 is coupled between the drain 136 and a voltage supply VDD. A second resistor 152 is coupled between the drain 144 and the voltage supply VDD. The source 140 and the source 146 are coupled to a voltage level such as ground 154.

The gate 134 is coupled to the first electrode 10 and ground 154 is coupled to the second electrode 12. Hence, a combination of one or more molecules 156 as described earlier is connected between the gate 134 and ground 154.

A first reference voltage 158 is applied to the gate 134. A second reference voltage 160 is applied to the gate 142. An electrical measurement to sense for a binding event can be performed by sensing a voltage at the drain 136, a voltage at the drain 144, or a voltage difference between the drain 136 and the drain 144.

Figure 7:
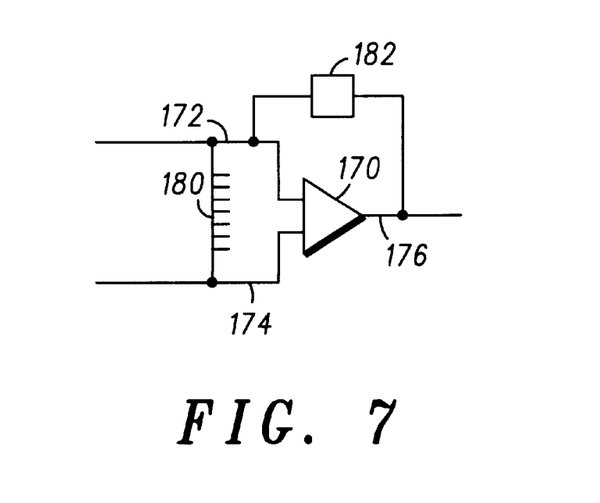
FIG. 7 is schematic, block diagram of another embodiment of a circuit used in the meter for molecular sensing.

FIG. 7 is a schematic, block diagram of another embodiment of a circuit used in the meter 46 for molecular sensing. The circuit includes a differential amplifier such as an operational amplifier 170 having a first input 172, a second input 174, and an output 176. A combination of one or more molecules 180 as described earlier can be connected between the first input 172 and the second input 174. Optionally, an impedance element 182 such as a resistor is connected between the first input 172 and the output 176. A signal indicative of a binding event is produced at the output 176 in response to an input signal (e.g. a voltage or a current) applied to at least one of the first input 172 and the second input 174.

As an alternative to the embodiment of FIG. 7, the combination of one or more molecules 180 can be electrically connected in a feedback loop between the first input 172 and the output 176, or can be electrically connected between a signal source and one of the first input 172 and the second input 174.

Thus, there has been described herein several embodiments including preferred embodiments of a molecular sensing apparatus and method.

Because the various embodiments of the present invention use molecules which are both bound to and electrically coupled to sensing electrodes, they provide a significant improvement in that a direct conductance measurement can be made across the sensing electrodes to sense for single-stranded DNA/RNA and double-stranded DNA/RNA.

It will be apparent to those skilled in the art that, the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A molecular sensing apparatus comprising:
   a first electrode;
   a second electrode;
   a first molecule having a first chain of nucleic bases and a first group, the first group bound to the first electrode;
   a second molecule having a second chain of nucleic bases and a second group, the second group bound to the second electrode; and
   a third molecule bound to the first molecule and the second molecule.

2. The molecular sensing apparatus of claim 1 wherein the first group and the second group are electrically conductive.

3. The molecular sensing apparatus of claim 1 wherein at least one of the first group and the second group comprises sulfur.

4. The molecular sensing apparatus of claim 1 wherein the third molecule comprises a first complementary chain of nucleic bases bound to the first chain of nucleic bases and a second complementary chain of nucleic bases bound to the second chain of nucleic bases.

5. The molecular sensing apparatus of claim 4 wherein the third molecule comprises a third chain of nucleic bases disposed between the first complementary chain of nucleic bases and the second complementary chain of nucleic bases.

6. The molecular sensing apparatus of claim 5 further comprising a fourth molecule bound to the third molecule, the fourth molecule having a third complementary chain of nucleic bases bound to the third chain of nucleic bases of the third molecule.

7. The molecular sensing apparatus of claim 1 wherein the first electrode and the second electrode are formed of a metal.

8. The molecular sensing apparatus of claim 7 wherein the first electrode and the second electrode are formed of gold.

9. The molecular sensing apparatus of claim 1 further comprising a substrate to support the first electrode and the second electrode, wherein the first electrode and the second electrode are integrated with the substrate.

10. The molecular sensing apparatus of claim 1 wherein the first electrode comprises a first surface to which the first molecule is bound, wherein the second electrode comprises a second surface to which the second molecule is bound, and wherein the first surface and the second surface are coplanar.

11. The molecular sensing apparatus of claim 1 further comprising a meter electrically coupled to the first electrode and the second electrode.

12. The molecular sensing apparatus of claim 11 wherein the first electrode and the second electrode provide a first electrode pair, the molecular sensing apparatus further comprising a second electrode pair similar to the first electrode pair, wherein the meter is electrically coupled to the second electrode pair.

13. The molecular sensing apparatus of claim 1 wherein at least one of the first electrode and the second electrode comprises a semiconducting material.

14. The molecular sensing apparatus of claim 1 wherein at least one of the first group and the second group is a silane group.

15. A molecular sensing apparatus comprising:
   a first electrode having a first surface;
   second electrode having a second surface coplanar to the first surface;
   a first molecule having a first chain of nucleic bases and a first end group, the first end group bound to the first surface of the first electrode;
   a second molecule having a second chain of nucleic bases and a second end group, the second end group bound to the second surface of the second electrode; and
   a third molecule having a first complementary chain of nucleic bases bound to the first chain of nucleic bases of the first molecule, a second complementary chain of nucleic bases bound to the second chain of nucleic bases of the second molecule, and a third chain of nucleic bases disposed between the first complementary chain of nucleic bases and the second complementary chain of nucleic bases.

16. The molecular sensing apparatus of claim 1 wherein at least one of the first group and the second group comprises selenium.

17. The molecular sensing apparatus of claim 1 wherein at least one of the first group and the second group comprises tellurium.

* * * * *